(12) United States Patent
Bilton

(10) Patent No.: US 9,347,930 B2
(45) Date of Patent: May 24, 2016

(54) DISPENSING MECHANISM FOR TEST STRIPS

(71) Applicant: SANOFI-AVENTIS DEUTSCHLAND GMBH, Frankfurt am Main (DE)

(72) Inventor: Simon Lewis Bilton, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/763,871

(22) PCT Filed: Jan. 30, 2014

(86) PCT No.: PCT/EP2014/051796
§ 371 (c)(1),
(2) Date: Jul. 28, 2015

(87) PCT Pub. No.: WO2014/118273
PCT Pub. Date: Aug. 7, 2014

(65) Prior Publication Data
US 2015/0369792 A1     Dec. 24, 2015

(30) Foreign Application Priority Data
Feb. 1, 2013   (EP) .................................... 13153727

(51) Int. Cl.
*B01L 9/00*     (2006.01)
*G01N 33/487*   (2006.01)

(52) U.S. Cl.
CPC ................................ *G01N 33/48757* (2013.01)

(58) Field of Classification Search
CPC ...................... B65D 83/0829; G01N 33/48757
See application file for complete search history.

(56) References Cited

U.S. PATENT DOCUMENTS

2007/0264165 A1   11/2007   Chan et al.
2011/0278321 A1   11/2011   Chan et al.

FOREIGN PATENT DOCUMENTS

EP          0749332         5/2005

OTHER PUBLICATIONS

International Search Report for Int. App. No. PCT/EP2014/051796, completed Feb. 19, 2014.

*Primary Examiner* — Leslie A Nicholson, III
*Assistant Examiner* — Ayodeji Ojofeitimi
(74) *Attorney, Agent, or Firm* — McDonnell Boehnen Hulbert & Berghoff LLP

(57) ABSTRACT

A dispensing mechanism for dispensing measurement strips is presented having a strip cartridge with an enclosure for retaining a plurality of measurement strips and a dispensing slot for dispensing one measurement strip at a time, a spring rotatably arranged with respect to the strip cartridge, the spring comprising at least one engagement section adapted to engage one of the measurement strips at a time and move it out of the dispensing slot when the spring is rotated, and a guide slot arranged in the strip cartridge for guiding the engagement section of the spring as the spring is rotated.

15 Claims, 4 Drawing Sheets

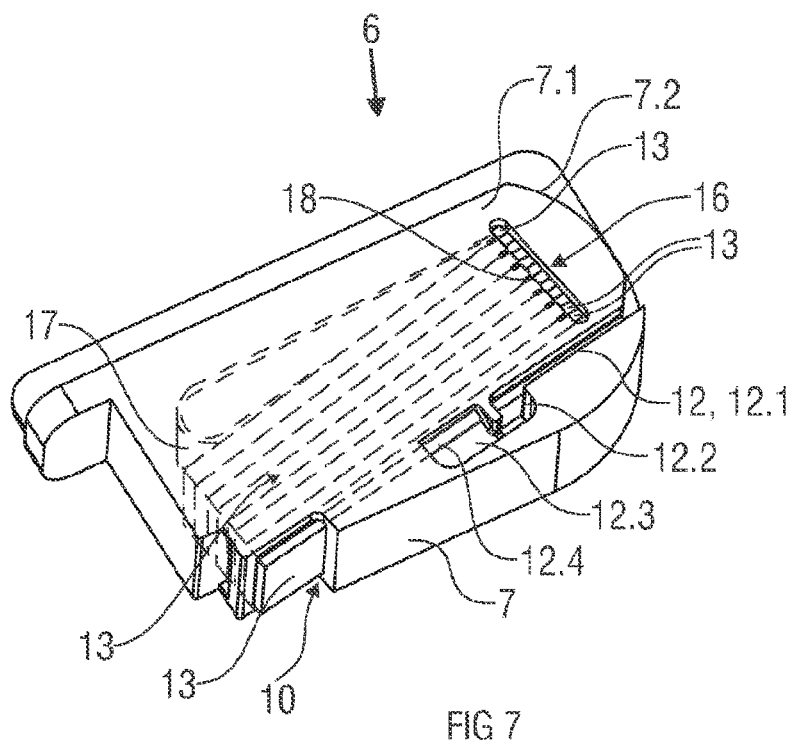

DISPENSING MECHANISM FOR TEST STRIPS

CROSS REFERENCE TO RELATED APPLICATIONS

The present application is a U.S. National Phase Application pursuant to 35 U.S.C. §371 of International Application No. PCT/EP2014/051796 filed Jan. 30, 2014, which claims priority to European Patent Application No. 13153727.6 filed Feb. 1, 2013. The entire disclosure contents of these applications are herewith incorporated by reference into the present application.

TECHNICAL FIELD

The invention relates to a dispensing mechanism for dispensing measurement strips.

BACKGROUND

Blood glucose measurement devices are arranged to determine blood glucose values by analyzing blood glucose measurement strips with a patient's blood sample. For ease of use it may be desirable to provide a supply of blood glucose measurement strips in a readily accessible form.

EP 0 749 332 B1 discloses a medication delivery device with a microprocessor and characteristic monitor comprising a storage area including a leaf spring mechanism and a slidable test strip supply button. Test strips are loaded into the storage area of the cap through the opening produced when the closed end of the cap is removed. The user presses the leaf spring mechanism down towards the center of the cap away from the supply button, and the test strips are then inserted between the leaf spring mechanism and the supply button. The leaf spring places the test strips under sufficient pressure such that a single test strip is ejected from the end of the cap next to the pen-type injector whenever the supply button is slid towards the open end of the cap. Once a test strip is ejected, the supply button is slid back towards the closed end of the cap and the next test strip is pressed into position to be ejected with the next sliding of the supply button.

SUMMARY

It is an object of the present invention to provide an improved dispensing mechanism for dispensing measurement strips.

The object is achieved by a dispensing mechanism according to claim 1.

Preferred embodiments of the invention are given in the dependent claims.

According to the invention a dispensing mechanism for dispensing measurement strips comprises:
- a strip cartridge with an enclosure for retaining a plurality of measurement strips and a dispensing slot for dispensing one measurement strip at a time,
- a spring rotatably arranged with respect to the strip cartridge, the spring comprising at least one engagement section adapted to engage one of the measurement strips at a time and move it out of the dispensing slot when the spring is rotated,
- a guide slot arranged in the strip cartridge for guiding the engagement section of the spring as the spring is rotated.

A user may rotate the spring in order to dispense a measurement strip. Other than in conventional dispensers the user does not have to reverse the direction of a dispense button to prepare the next measurement strip. Instead, it is sufficient to further rotate the spring in order to dispense the next measurement strip.

The dispensing mechanism may be used for blood glucose measurement strips or for other types of measurement strips for medical or non-medical use.

In an exemplary embodiment the guide slot comprises a first section in parallel to and in the vicinity of the measurement strips such that the engagement section engages one of the blood glucose measurement strips when within the first section, wherein the first section is followed by a second section directed to allow the engagement section to move out of engagement with the measurement strips. This design of the guide slot provides a one-way feature to the dispensing mechanism preventing a user from reversing the rotational direction of the spring once the engagement section of the spring has reached the second section of the guide slot.

In an exemplary embodiment the guide slot comprises a ramp for guiding the engagement section out of the guide slot when rotated further after having disengaged the measurement strip. This allows the engagement section to cross the path of the measurement strip in a different plane thus avoiding further interference after the measurement strip has been placed in a position in which the user can remove it from the dispensing mechanism.

In an exemplary embodiment the spring is arranged as a wire spring. The wire spring may be substantially Z-shaped with a substantially straight inner section connected to two substantially straight outer sections, wherein a respective engagement section is arranged at an end of each outer section, wherein the engagement section is bent so as to point at substantially right angles out of a plane, in which the inner section and the outer sections are arranged. This allows for dispensing one measurement strip by a 180° rotation of the spring.

In an exemplary embodiment the outer sections are connected to the inner section through respective curved sections and/or the engagement sections are connected to the outer sections by respective curved sections. Both the curved and the straight sections allow for storing energy in the spring by deforming them.

In an exemplary embodiment a thumb wheel is coupled to the spring for rotation. The thumb wheel facilitates rotation of the spring as it can be more easily engaged by a user's thumb or finger.

In an exemplary embodiment the inner section of the wire spring is held in a transversal slot or bore within the thumb wheel.

In an exemplary embodiment the guide slot is arranged in a surface of the strip cartridge, wherein the ramp is arranged to guide the engagement section out of the guide slot onto the surface. The surface maintains the engagement section out of a plane in which it could interfere with the plurality of measurement strips until the engagement section has been rotated across them.

In an exemplary embodiment the first section is substantially straight so as to store energy in the spring on translation of the engagement section through the first section such that the stored energy is released and moves the engagement section out of engagement with the measurement strip once it reaches the second section. The energy is stored in the spring as the engagement section would naturally follow a circular path when rotated but is forced to follow a linear path as long as it is located in the first section of the guide slot.

In an exemplary embodiment a second spring is arranged to bias the plurality of measurement strips towards the guide slot such that a new measurement strip automatically falls in place as soon as the preceding one has been moved out of the way by the engagement section of the spring and/or by the user.

In an exemplary embodiment a volume indicator is arranged as an aperture or window in the strip cartridge. This allows a user to estimate how long the supply of measurement strips will last.

In an exemplary embodiment the thumb wheel comprises a grip profile in order to improve handling of the thumb wheel.

In an exemplary embodiment the dispensing mechanism is arranged within a cap arranged to be assembled to a measurement device. The supply of measurement strips is thus readily available to the user as opposed to supplies stored separately from the measurement device.

In an exemplary embodiment the measurement device is a blood glucose measurement device comprising a cap with the dispensing mechanism.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 7 is a schematic perspective view of an exemplary embodiment of the dispensing mechanism with a volume indicator.

Corresponding parts are marked with the same reference symbols in all figures.

DETAILED DESCRIPTION

Figure 1:
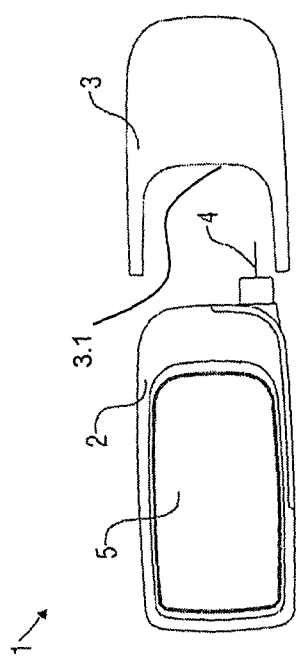
FIG. 1 is a schematic view of an exemplary embodiment of blood glucose measurement device comprising a cap.

FIG. 1 is a schematic view of an exemplary embodiment of blood glucose measurement device 1 comprising a body 2 and a removable cap 3. The blood glucose measurement device 1 is integrated with a drug delivery device arranged to mount an injection needle 4. Furthermore, the blood glucose measurement device 1 comprises an interface 5 for displaying information related to a blood glucose measurement to a user and allowing the user to operate the blood glucose measurement device 1. The interface 5 may be arranged as a touch screen. The blood glucose measurement device 1 furthermore comprises a slot or port (not illustrated) for inserting a blood glucose measurement strip and analyzing it.

Figure 2:
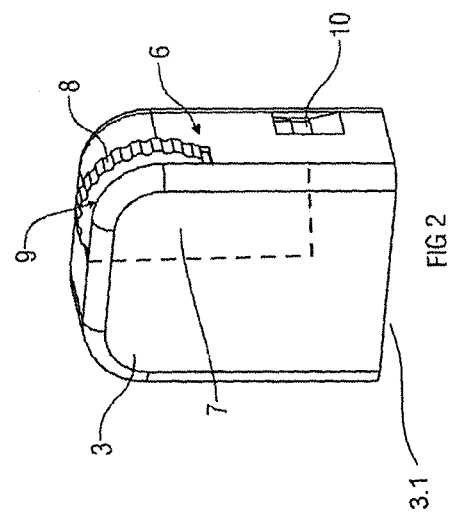
FIG. 2 is a schematic perspective view of an exemplary embodiment of the cap with a dispensing mechanism for blood glucose measurement strips.

FIG. 2 is a schematic perspective view of an exemplary embodiment of the cap 3 with an integrated dispensing mechanism 6 for blood glucose measurement strips. The dispensing mechanism 6 is arranged to retain a strip cartridge 7 comprising a plurality of blood glucose measurement strips. A thumb wheel 8 laterally protrudes through an opening 9 in an outer surface of the cap 3. A dispensing slot 10 is laterally arranged in the cap 3 for dispensing one blood glucose measurement strip at a time. The thumb wheel 8 is profiled so as to enable a user to rotate it with their finger, e.g. a thumb. As a result of this rotation a single blood glucose measurement strip is ejected from the dispensing slot 10.

Figure 3:
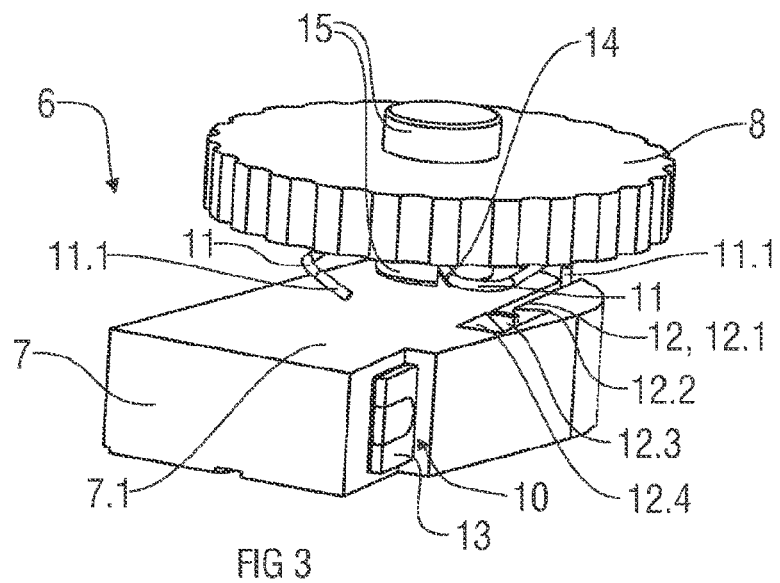
FIG. 3 is a schematic perspective view of the dispensing mechanism.

FIG. 3 is a schematic perspective view of the dispensing mechanism 6. The thumb wheel 8 is rotationally coupled to a wire spring 11. As the thumb wheel 8 is rotated, one engagement section 11.1 of the wire spring 11 enters a guide slot 12 in a surface 7.1 of the strip cartridge 7 facing the thumb wheel 8 and acts on a back face of a single blood glucose measurement strip 13 which is partially visible in FIG. 3.

Figure 4:
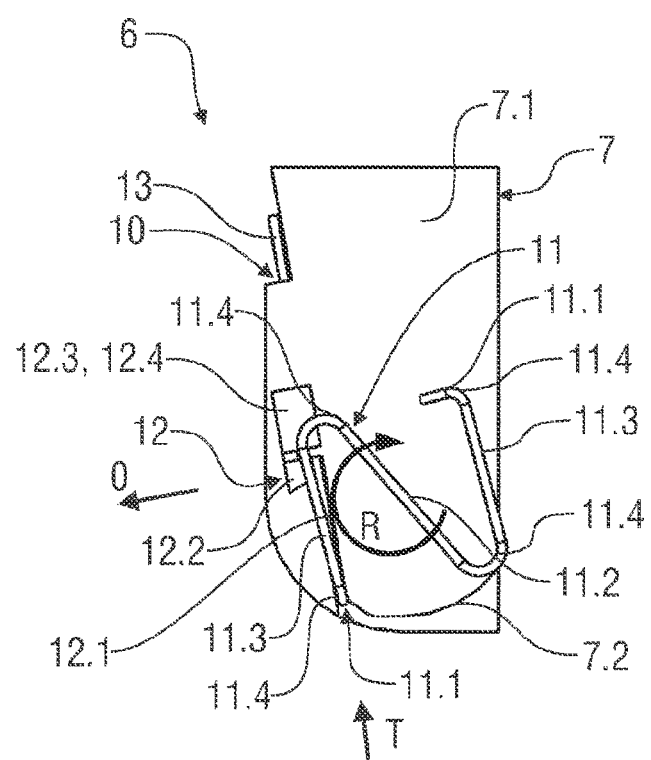
FIG. 4 is a schematic detail view of the dispensing mechanism in a first position.

FIG. 4 is a schematic detail view of the dispensing mechanism 6 in a first position. The wire spring 11 is substantially Z-shaped with a substantially straight inner section 11.2 connected to two substantially straight outer sections 11.3. At an end of the outer sections 11.3 a respective engagement section 11.1 is arranged. While the inner section 11.2 and the outer sections 11.3 are substantially arranged within one plane the engagement section 11.1 is bent so as to point at substantially right angles out of this plane and into the guide slot 12. The outer sections 11.3 may be connected to the inner section 11.2 through respective curved sections 11.4. The engagement sections 11.1 may likewise be connected to the outer sections 11.3 by respective curved sections 11.4. The inner section 11.2 is held in a transversal slot 14 or bore within a hub 15 (cf. FIG. 3) of the thumb wheel 8 such that the inner section 11.2 is coupled to the thumb wheel 8 in rotation.

The guide slot 12 comprises a substantially straight first section 12.1 pointing in a tangential direction T with respect to the hub 15 in parallel to and in the vicinity of the plurality of blood glucose measurement strips 13 such that the engagement section 11.1 engages one of the blood glucose measurement strips 13 when within the first section 12.1. The first section 12.1 is followed by a second section 12.2 substantially pointing in an outward direction O, i.e. substantially arranged transversally to the first section 12.1 so as to allow the engagement section 11.1 to relax and move away and out of engagement with the blood glucose measurement strips 13. The transversal arrangement of the second section 12.2 provides a one-way feature preventing rotation of the thumb wheel 8 and wire spring 11 against the rotational direction R. The one-way functionality may be improved by directing the second section 12.2 at an acute angle relative to the first section 12.1 (as illustrated) instead of at right angles.

The second section 12.2 is followed by a third section 12.3 in parallel to the first section 12.1. The third section 12.3 comprises a ramp 12.4 for guiding the engagement section 11.1 out of the guide slot 12 onto the surface 7.1 of the strip cartridge 7 when rotated further by the thumb wheel 8.

The thumb wheel 8 has been omitted in FIGS. 4 to 7 for clarity.

In FIG. 4 the thumb wheel 8 has been rotated in a rotational direction R thereby causing one of the engagement sections 11.1 of the wire spring 11 to enter the guide slot 12 and to engage one of the blood glucose measurement strips 13 which is the most distant one of the plurality of blood glucose measurement strips 13 with respect to the hub 15. The other engagement section 11.1 is located on the surface 7.1 of the strip cartridge 7.

The user continues rotating the thumb wheel 8 thereby causing the engagement section 11.1 of the wire spring to travel up the first section 12.1 taking with it the blood glucose measurement strip 13. As the first section 12.1 is straight the engagement section 11.1 cannot follow a circular path as it would naturally do when relaxed. Instead, at least one of the inner section 11.2, the outer sections 11.3 and the curved sections 11.4 is resiliently deformed, hence energy is stored in the wire spring 11. As the engagement section 11.1 travels along the first section 12.1 it pushes the blood glucose measurement strip 13 out of the dispensing slot 10 sufficiently far that it may be gripped by the user.

Figure 5:
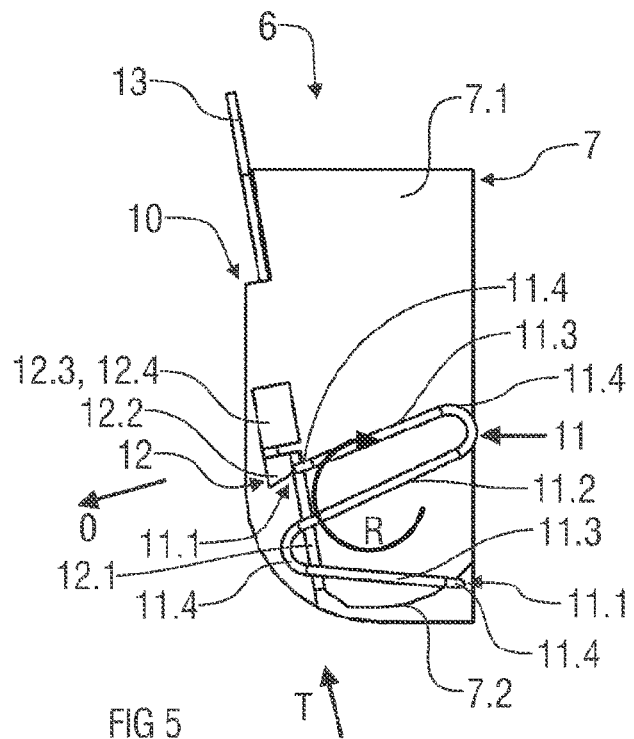
FIG. 5 is a schematic detail view of the dispensing mechanism in a second position.

FIG. 5 is a schematic detail view of the dispensing mechanism 6 in a second position. The engagement section 11.1 has traveled up the first section 12.1 of the guide slot 12 and reached the second section 12.2. The energy stored in the wire spring 11 causes the engagement section 11.1 to at least partially relax and travel along the second section 12.2 in the outward direction O disengaging the blood glucose measurement strip 13 and clearing the first section 12.1 to allow a subsequent blood glucose measurement strip 13 to fall in place, e.g. biased by a second spring. As soon as the engagement section 11.1 reaches the third section 12.3 the remaining energy stored in the wire spring 11 moves the engagement section 11.1 along the third section 12.3 in the tangential direction T until it reaches the ramp 12.4.

Figure 6:
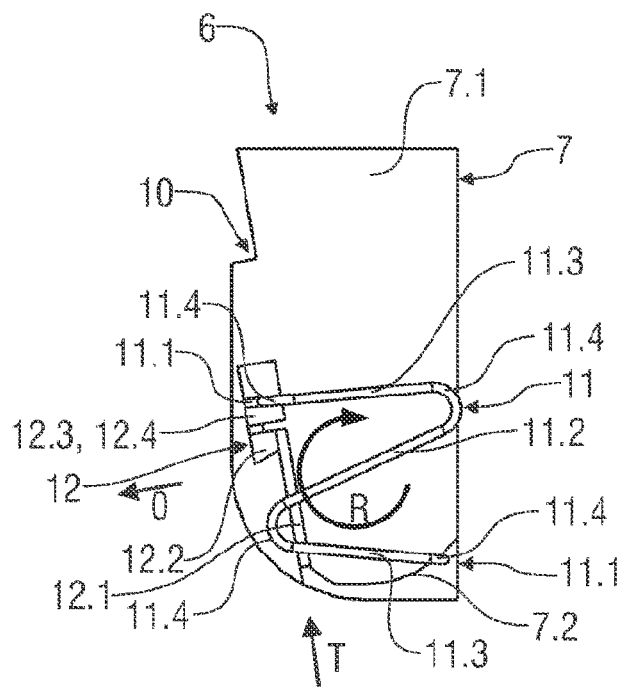
FIG. 6 is a schematic detail view of the dispensing mechanism in a third position.

FIG. 6 is a schematic detail view of the dispensing mechanism 6 in a third position, wherein the engagement section 11.1 has reached the ramp 12.4. Continued rotation of the thumb wheel 8 moves the engagement section 11.1 against the outward direction O up the ramp 12.4 such that the engagement section 11.1 is led out of the guide slot 12 and onto the surface 7.1 thus deflecting the adjacent outer section 11.3, the engagement section 11.1 and the related curved sections 11.4 and storing energy in the wire spring 11.

As the engagement section 11.1 has traveled up the ramp 12.4 and is located on the surface 7.1 the other engagement section 11.1 is about to enter the first section 12.1 of the guide slot 12 thus arriving in the first position as illustrated in FIG. 4 after a 180° rotation of the thumb wheel 8. The engagement sections 11.1 located on the surface 7.1 reaches the first position by travelling across the surface 7.1 until it reaches an edge of the surface 7.1 allowing it to move off the surface 7.1 such that the respective part of the wire spring 11 can relax. A curved portion 7.2 on the strip cartridge 7 may be arranged to allow the end section 11 to travel around the strip cartridge 7 towards the first position without interfering with the strip cartridge 7.

In the illustrated embodiment, the wire spring 11 has two engagement sections 11.1, so that a half rotation of the thumb wheel is sufficient to eject a single blood glucose measurement strip 13. However it can be envisaged that more complex spring arrangements could be used to achieve a smaller rotation of the thumb wheel 8 per blood glucose measurement strip 13.

FIG. 7 is a schematic perspective view of an exemplary embodiment of the dispensing mechanism 6 with a volume indicator 16. The thumb wheel 8 and the wire spring 11 have been omitted for clarity. The strip cartridge 7 comprises an enclosure containing the plurality of stacked blood glucose measurement strips 13 and a second spring 17. The second spring 17 is arranged to bias the plurality of blood glucose measurement strips 13 in the outward direction O to ensure that a new blood glucose measurement strip 13 falls in place once the previous one has been removed from the dispensing slot 10.

The strip cartridge 7 may be removably arranged within the cap 3 thus allowing the user to replace it with a new one when it has been emptied of blood glucose measurement strips 13.

The strip cartridge 7 may be accessible through an opening 3.1 in the cap 3 adapted to engage the body 2 of the blood glucose measurement device 1.

Likewise the strip cartridge 7 may be arranged to be opened to allow insertion of new blood glucose measurement strips 13. Likewise, new blood glucose measurement strips 13 maybe fed into the strip cartridge 7 through the dispensing slot 10 or an alternative aperture.

If the strip cartridge 7 is removably arranged within the cap 3 a push-push mechanism may be arranged to insert and remove the strip cartridge 7. This may simplify the insertion and removal of the strip cartridge 7.

In the exemplary embodiment illustrated in FIG. 7 the strip cartridge 7 comprises a volume indicator 16 to display how many blood glucose measurement strips 13 are left in the strip cartridge 7. The volume indicator 16 is arranged as an aperture or window in the surface 7.1, with a scale 18, to allow the user to view the blood glucose measurement strips 13 inside. As the blood glucose measurement strips 13 are removed one by one, the number of remaining blood glucose measurement strips 13 is visible through the aperture. In FIG. 7 the strip cartridge 7 contains a full set of blood glucose measurement strips 13.

In the embodiment illustrated in FIG. 1 the blood glucose measurement device 1 is integrated with a drug delivery device arranged to mount an injection needle 3. However, this is not a requirement. The blood glucose measurement device 1 could likewise be arranged without the drug delivery device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. Dispensing mechanism for dispensing measurement strips, comprising:
    a strip cartridge with an enclosure for retaining a plurality of measurement strips and a dispensing slot for dispensing one measurement strip at a time,
    a spring rotatably arranged with respect to the strip cartridge, the spring comprising at least one engagement section adapted to engage one of the measurement strips at a time and move it out of the dispensing slot when the spring is rotated,
    a guide slot arranged in the strip cartridge for guiding the engagement section of the spring as the spring is rotated.

2. The dispensing mechanism according to claim 1, wherein the guide slot comprises a first section in parallel to and in the vicinity of the measurement strips such that the engagement section engages one of the blood glucose measurement strips when within the first section, wherein the first section is followed by a second section directed to allow the engagement section to move out of engagement with the measurement strips.

3. The dispensing mechanism according to claim 2, wherein the guide slot comprises a ramp for guiding the engagement section out of the guide slot when rotated further after having disengaged the measurement strip.

4. The dispensing mechanism according to claim 1, wherein the spring is arranged as a wire spring.

5. The dispensing mechanism according to claim 4, wherein the wire spring is substantially Z-shaped with a substantially straight inner section connected to two substantially straight outer sections, wherein a respective engagement section is arranged at an end of each outer section, wherein the engagement section is bent so as to point at substantially right angles out of a plane, in which the inner section and the outer sections are arranged.

6. The dispensing mechanism according to claim 5, wherein the outer sections are connected to the inner section through respective curved sections and/or wherein the engagement sections are connected to the outer sections by respective curved sections.

7. The dispensing mechanism according to claim 1, wherein a thumb wheel is coupled to the spring for rotation.

8. The dispensing mechanism according to claim 7, wherein an inner section of the spring is held in a transversal slot or bore within the thumb wheel.

9. The dispensing mechanism according to claim 3, wherein the guide slot is arranged in a surface of the strip cartridge, wherein the ramp is arranged to guide the engagement section out of the guide slot onto the surface.

10. The dispensing mechanism according to claim 2, wherein the first section is substantially straight so as to store energy in the spring on translation of the engagement section through the first section such that the stored energy is released and moves the engagement section out of engagement with the measurement strip once it reaches the second section.

11. The dispensing mechanism according to claim 1, wherein a second spring is arranged to bias the plurality of measurement strips towards the guide slot.

12. The dispensing mechanism according to claim 1, wherein a volume indicator is arranged as an aperture or window in the strip cartridge.

13. The dispensing mechanism according to claim 7, wherein the thumb wheel comprises a grip profile.

14. A cap, arranged to be assembled to a measurement device, the cap comprising a dispensing mechanism according to claim 1.

15. A blood glucose measurement device, comprising a cap according to claim 14.

* * * * *